United States Patent [19]

Bertazzoli et al.

[11] 4,056,613

[45] Nov. 1, 1977

[54] METHOD OF REDUCING THE CARDIOTOXIC SIDE EFFECTS OF GLYCOSIDIC ANTHRACYCLINONES

[75] Inventors: Cesare Bertazzoli; Luisa Sala; Mario Ghione, all of Milan, Italy

[73] Assignee: Societa Farmaceutici Italia S.p.A., Milan, Italy

[21] Appl. No.: 704,508

[22] Filed: July 12, 1976

[30] Foreign Application Priority Data

July 21, 1975 United Kingdom ............... 32152/75

[51] Int. Cl.$^2$ ..................... A61K 37/48; A61K 31/70
[52] U.S. Cl. ........................................ 424/94; 424/180
[58] Field of Search .................................. 424/180, 94

[56] References Cited

PUBLICATIONS

Iwamoto et al., Biochem. & Biophy. Res. Commun., vol. 58, No. 3, 1974, pp. 633-638.
Chemical Abstracts 83: 172462g, (Aug. 1975).
Chemical Abstracts 84: 359h, (Aug. 1975).

*Primary Examiner*—Jerome D. Goldberg
*Attorney, Agent, or Firm*—Hubbell, Cohen, Stiefel & Gross

[57] ABSTRACT

The cardiotoxic effects incident to the use of glycosidic anthracyclinones such as adriamycin, daunomycin, etc., in antitumor therapy, are substantially reduced by administering to a host undergoing such therapy, and effective amount of coenzymes Q, particularly Co-$Q_{10}$ (Ubiquinone $Q_{10}$).

1 Claim, No Drawings

METHOD OF REDUCING THE CARDIOTOXIC SIDE EFFECTS OF GLYCOSIDIC ANTHRACYCLINONES

BACKGROUND OF THE INVENTION

1. Field of the Invention

The invention relates to antitumor therapy and in particular, to the reduction of the cordiotoxic side effects that usually occur when a host is undergoing antitumor therapy with a glycosidic anthracyclinone such as the known antibiotics adriamycin and daunomycin.

2. The Prior Art

Data from in vitro experiments which have been reported in the literature (Iwamoto et al., Biochem. Biophys. Res. Comm., 58, 633–638 (1974)) indicate that glycosidic anthracyclinones inhibit $Co-Q_{10}$ enzymes in the electron transfer processes that occur during cell respiration. These data therefore support the hypothesis that pathogenesis of the cordiotoxic effects of glycosidic anthracyclinones may be directly or indirectly ascribed to the inhibition of electron transfer processes and that it is possible to antagonize these effects by supplying exogenous CoQ (Ubiquinone), the chemical structure of which is based on the 2,3-dimethoxy-5-methylbenzoquinone nucleus with a terpenoid side chain in the 6 position containing monounsaturated isoprenoid units (K. Folkers, Ciba Foundation Symposium on Quinones in Electron Transport, pg. 100–129 (Churchill, London, 1961)).

SUMMARY OF THE INVENTION

The present invention provides a method to be used during the treatment of tumoral diseases by the well known antitumor glycosidic anthracyclinones such as adriamycin, daunomycin, etc. This method counteracts the cardiotoxic effects, which are in some case irreversible and fatal, and which may occur after prolonged treatment with high cumulative doses of the above mentioned antibiotics.

The method comprises administering to a host undergoing antitumor therapy with said antibiotics, an effective amount of coenzymes-Q, preferably, coenzyme $Q_{10}$.

To demonstrate and confirm the fact that the method is operative, a suitable animal model of the cardiomyopathy induced by administration of glycosidic anthracyclinones was developed by us. It has now been found, and the invention is based on the fact that the administration of coenzymes Q and particularly of $Co-Q_{10}$ (Ubiquinone $Q_{10}$), at low dosage, and following a particular scheme of administration, almost completely counteracts in vivo the side-effects induced by the glycosidic anthracyclinones by reducing both the incidence and severity of the cardiomyocell degeneration consisting mainly in intracellular vacuolation, disorganization and fusion of contractile elements and cytoplasmatic coagulation or dissolution.

DESCRIPTION OF THE PREFERRED EMBODIMENTS

The following examples, the results of which are given in the Table serve to illustrate the invention, but they are not intended to limit it.

The experiments were carried out on eight adult male NZW rabbits which were treated i.v. every morning, for a five day week with 0.1 mg. of Ubiquinone $Q_{10}$ per kg. of body weight (suspended in 1 ml./kg. of saline solution). Three days after the start of the Ubiquinone treatment, the same animals were also treated i.v. daily, in the afternoon, with 0.8 mg. of adriamycin per kg. of body weight, on three consecutive days every week (in 2 ml./kg. of saline solution), for a total of three months. A second group of eight animals was similarly treated with adriamycin but with saline instead of the Ubiquinone suspension. Five animals, treated only with saline, served as controls. After three months of treatment all the rabbits were sacrificed. Mean values of biochemical, hematological and cardiological data (ECG recording) are given in the following Table.

TABLE

Final Examination - Mean Values and Standard Error (±)

| Groups | HEMATOLOGY | | | ECG PATTERNS | | | BLOOD BIOCHEMISTRY | | | | | | | | URINE |
|---|---|---|---|---|---|---|---|---|---|---|---|---|---|---|---|
| | Erythrocytes (N°/mm³ ×1000) | Leukocytes (No./mm³ ×100) | Hemoglobin (g%) | Tachycardia (beats/min) | T wave inversion | No. of rabbits with | BUN (mg%) | Creatinine (mg%) | Total cholesterol (mg%) | Fibrinogen (mg%) | Albumin | α | β | γ | Proteins (mg%) |
| | | | | | | | | | | | | Serum proteins (fraction as %) | | | |
| C | 6335 ±155 | 140 ±12 | 14.2 ±0.35 | 225 ±6.71 | | 0 | 27 ±1.05 | 1.72 ±0.10 | 31.80 ±2.82 | 332 ±31.81 | 66 ±0.86 | 9 ±0.32 | 16 ±0.45 | 9 ±0.37 | 2.58 ±0.29 |
| A | 5216 ±377 | 93 ±10 | 11.5 ±0.40 | 284 ±19.08 | 5 | | 44.2 ±5.24 | 2.41 ±0.15 | 81.33 ±27.17 | 530 ±95.92 | 51 ±6.29 | 15 ±4.92 | 27 ±1.99 | 7* ±0.49 | 93.7 ±43.89 |
| A+U | 5668* ±293 | 133* ±17 | 12.8* ±0.47 | 227** ±12.00 | 1*** | | 22.9** ±1.50 | 1.88** ±0.16 | 80.00* ±29.46 | 579* ±125.14 | 53* ±4.65 | 13* ±2.78 | 27* ±2.20 | 7* ±0.89 | 59.74* ±41.00 |

C = controls
A = adriamycin
A+U = adriamycin plus ubiquinone
* = not significantly different from A group for P-0.05 (Student's "t")
** = significantly different from A group for P-0.05 (Student's "t")
*** = significantly different from A group for P-0.05 (X² test)

It can be seen that the treatment with Ubiquinone almost completely counteracts the cordiotoxic effects of adriamycin on the ECG patterns (i.e. tachycardia and inversion of T wave).

In addition, Ubiquinone counteracts some of the toxic effects involving biochemical parameters such as the increase of BUN and blood creatinine while it does not have any action on the increase of blood total cholesterol, fibrinogen, $\alpha$ and $\beta$ globulin fractions and on proteinuria. Slight, but not significant, effects are seen also on bone marrow depression induced by adriamycin. Moreover, histological examination of the heart of all the adriamycin treated rabbits revealed very extensive and severe myocell degeneration. In four rabbits treated simultaneously with adriamycin and Ubiquinone the heart appeared either normal or only slightly damaged on histological examination. The remaining four rabbits showed significantly less severe and extensive changes when compared with those rabbits receiving adriamycin only. In conclusion, these experiments show that administration of Ubiquinone at low dosage, effectively counteracts both the incidence and severity of the cardiomyopathy which has, until now limited the usefulness of glycosidic anthracyclinones in the therapy of tumoral diseases.

Variations and modifications can, of course, be made without departing from the spirit and scope of the invention.

Having thus described our invention, what we desire to secure by Letters Patent and hereby claim is:

1. A method for reducing the cardiotoxic effects of adriamycin which comprises administering to an animal in need thereof an effective amount of $CoQ_{10}$ to inhibit the cardiotoxic effects of adriamycin.

* * * * *

UNITED STATES PATENT OFFICE
CERTIFICATE OF CORRECTION

Patent No. 4,056,613          Dated November 1, 1977

Inventor(s) Cesare Bertazzoli et al

It is certified that error appears in the above-identified patent and that said Letters Patent are hereby corrected as shown below:

Title page, right side, line 4 of Abstract: "therapy, and" should read -- therapy, an --.

Column 1, line 8: "cordiotoxic" should read -- cardiotoxic --; line 20: "cordiotoxic" should read -- cardiotoxic --; line 38: "case" should read -- cases --.

Column 3, line 2: "cordiotoxic" should read -- cardiotoxic --.

Column 4, line 2 of claim 1: "adriamycin which comprising" should read -- adriamycin comprising --.

Signed and Sealed this

Twenty-fifth Day of April 1978

[SEAL]

Attest:

RUTH C. MASON          LUTRELLE F. PARKER
*Attesting Officer*          *Acting Commissioner of Patents and Trademarks*